(12) United States Patent
Langaee et al.

(10) Patent No.: US 9,765,393 B2
(45) Date of Patent: Sep. 19, 2017

(54) METHODS, ASSAYS, AND KITS RELATED TO DICHLOROACETATE (DCA)

(75) Inventors: Taimour Langaee, Gainesville, FL (US); Peter W. Stacpoole, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 636 days.

(21) Appl. No.: 13/703,990

(22) PCT Filed: Jun. 14, 2011

(86) PCT No.: PCT/US2011/040282
§ 371 (c)(1),
(2), (4) Date: Dec. 13, 2012

(87) PCT Pub. No.: WO2011/159658
PCT Pub. Date: Dec. 22, 2011

(65) Prior Publication Data
US 2013/0090382 A1    Apr. 11, 2013

Related U.S. Application Data

(60) Provisional application No. 61/354,453, filed on Jun. 14, 2010.

(51) Int. Cl.
*C07H 21/02* (2006.01)
*C07H 21/04* (2006.01)
*C12Q 1/68* (2006.01)

(52) U.S. Cl.
CPC ......... *C12Q 1/6869* (2013.01); *C12Q 1/6883* (2013.01); *C12Q 2600/106* (2013.01); *C12Q 2600/156* (2013.01); *C12Q 2600/172* (2013.01)

(58) Field of Classification Search
CPC ............ C12Q 1/6883; C12Q 2600/106; C12Q 2600/156; C12Q 1/6869; C12Q 2600/172; C12Q 1/6876
See application file for complete search history.

(56) References Cited

U.S. PATENT DOCUMENTS

2001/0053519 A1*  12/2001  Fodor et al. ................. 435/6

FOREIGN PATENT DOCUMENTS

| EP | 1731146 A1 | 12/2006 |
|---|---|---|
| WO | 9917763 | 4/1999 |
| WO | 2006105537 A2 | 10/2006 |
| WO | 2007030944 A2 | 3/2007 |

OTHER PUBLICATIONS

Illumina SNP Genotyping product information sheet for Sentrix HumanHap300 Genotyping BeadChip, 2006, Pub. No. 370-2006-007 from Illumina, Inc., pp. 1-4.*
Ahern H. The Scientist (Jul. 24, 1995), pp. 20 and 22.*
dbSNP cluster report for rs1046428, from www.ncbi.nlm.nih.gov, printed on Feb. 6, 2014, pp. 1-5.*
dbSNP cluster report for rs7972, from www.ncbi.nlm.nih.gov, printed on Feb. 6, 2014, pp. 1-4.*
dbSNP cluster report for rs7975, from www.ncbi.nlm.nih.gov, printed on Feb. 6, 2014, pp. 1-5.*
The International Search Report and Written Opinion dated Feb. 27, 2012.
Stacpoole, et al., "Role of Dichloroacetate in the Treatment of Genetic Mitochondrial Diseases," Advanced Drug Delivery Reviews, vol. 60(13-14), pp. 1478-1487, Jul. 4, 2008.
Tzeng, et al., "Polymorphism-and Species-Dependent Inactivation of Glutathione Transferase Zeta by Dichloroacetate," Chemical Research in Toxicology, vol. 13(4), pp. 231-236 (Apr. 2006).
Lantum, et al., Kinetics of the Biotransformation of Maleylacetone and Chlorofluoracetic Acid by Polymorphic Variants of Human Glutathione Transferase Zeta(hGSTZ1-1), Chemical Research in Toxicology, vol. 15, pp. 957-963 (Jul. 2002).
Blackburn, et al., "Discovery of a Functional Polymorphism in Human Glutathione Transferase Zeta by Expressed Sequence Tag Database Analysis," Pharmacogenetics, vol. 10(1), pp. 49-57 (Feb. 2000).

* cited by examiner

*Primary Examiner* — Stephen Kapushoc
(74) *Attorney, Agent, or Firm* — Thomas|Horstemeyer, LLP

(57) ABSTRACT

Embodiments of the present disclosure provide for methods, assays, and kits for predicting dosing for subjects. In addition, embodiments of the present disclosure include methods, assays, and kits, of determining if a patient can effectively metabolize one or both of phenylalanine and tryrosine.

11 Claims, 11 Drawing Sheets

Table 1. Pharmacokinetics of 25 mg/kg 1, 2- 13C-DCA after 1 and 5 Doses.

| | Subject Age/Sex/Race | Genotype GSTz1/MAAI | Cmax (μg/ml) | AUC (μg/ml * min) | t1/2 (min) | CL (ml/min) | After 5th DCA Dose Cmax (μg/ml) | AUC (μg/ml * min) | t1/2 (min) | CL (ml/min) |
|---|---|---|---|---|---|---|---|---|---|---|
| | | EGT Carriers | | | | | | | | |
| 1 | 24/F/White | EGT/EGT | 27.2 | 8211 | 79 | 3.04 | 36.1 | 21703 | 305 | 1.15 (2.6)* |
| 2 | 25/F/White | EGT/EGT | 60.3 | 8644 | 97 | 2.89 | 27.9 | 11705 | 218 | 2.14 (1.4) |
| 3 | 24/M/White | EGT/EGT | 19.4 | 1313 | 46 | 19.05 | 28.5 | 7899 | 122 | 3.17 (6.0) |
| 4 | 23/M/Black | EGT/EGT | 41.5 | 3689 | 37 | 6.78 | 32.7 | 12612 | 232 | 1.98 (3.4) |
| 5 | 26/F/Asian | EGT/KGT | 20.4 | 2622 | 36 | 9.54 | 22.6 | 11783 | 310 | 2.12 (4.5) |
| 6 | 23/F/Black | EGT/KRT | 18.1 | 1423 | 80 | 17.57 | 28.5 | 7934 | 126 | 3.15 (5.6) |
| 7 | 25/F/White | EGT/KRT | 14.4 | 1538 | 102 | 16.25 | 22.8 | 13715 | 323 | 1.82 (8.9) |
| | | EGT Non-carriers | | | | | | | | |
| 8 | 25/F/White | KRT/KGT | 31.8 | 3366 | 41 | 7.43 | 27 | 11746 | 243 | 2.13 (3.5) |
| 9 | 37/M/White | KGT/KGT | 24.7 | 4048 | 102 | 6.18 | 26.5 | 29214 | 727 | 0.86 (7.2) |
| 10 | 33/F/White | KRT/KRT | 12.4 | 1493 | 96 | 16.74 | 33.1 | 79525 | 1592 | 0.31 (54.0) |
| 11 | 21/M/White | KRT/EGM | 49.4 | 5301 | 47 | 4.72 | 35.3 | 98683 | 1774 | 0.25 (18.9) |
| 12 | 26/M/White | KGM/KGT | 27.8 | 78165 | 1264 | 0.32 | 40.8 | 302977 | 5408 | 0.08 (4.0) |

Abbreviations: Cmax, maximum plasma concentration; AUC, area under plasma concentration curve; t1/2, elimination half-life; CL, plasma clearance.
* Values in parentheses denote fold-change in CL between first and fifth doses.

FIG. 6

Table 2. Urinary Levels of $^{12}$C-DCA and Maleylacetone after 5 Days of 25 mg/kg/d DCA.

| Subject | Genotype | DCA (mmol/mol Cr) | MA (mmol/mol Cr) |
|---|---|---|---|
| 9 | KGT/KGT | 7.4 | 3.3 |
| 11 | KRT/KRT | 6.1 | 4.7 |
| 10 | KRT/EGM | 122.2 | 8.5 |
| 12 | KGM/KGT | 75.7 | 12.4 |

Subjects from Table 1. Urine was collected during the final 12 hours of day 5 of DCA administration.

Abbreviations: MA, maleylacetone; Cr, creatinine.

FIG. 7

Table 3. Pharmacokinetics of 2.5 μg/kg of 1, 2- $^{13}$C-DCA after 1 and 5 Doses.

| Subject | GSTz1/MAAI Genotype | After 1st DCA Dose | | | | After 5th DCA Dose | | | |
|---|---|---|---|---|---|---|---|---|---|
| | | Cmax (ng) | AUC (ng/ml * min) | t1/2 (min) | CL (ml/min) | Cmax (ng/ml) | AUC (ng/ml * min) | t1/2 (min) | CL (ml/min) |
| | EGT carriers | | | | | | | | |
| 1 | EGT/EGT | 6.7 | 331 | 62 | 7.5 | 4.0 | 873 | 62.2 | 2.9 |
| 2 | EGT/EGT | 5.8 | 305 | 56 | 8.2 | 4.7 | 814 | 91.4 | 3.1 |
| 3 | EGT/EGT | 6.2 | 376 | 76 | 6.7 | 5.7 | 998 | 50.5 | 2.5 |
| 4 | EGT/EGT | 10.5 | 817 | 71 | 3.1 | 7.9 | 1300 | 80.9 | 1.9 |
| 5 | EGT/KGT | 7.5 | 869 | 67 | 2.9 | 5.0 | 974 | 74.3 | 2.6 |
| 6 | EGT/KRT | 8.3 | 497 | 61 | 5.0 | 7.6 | 1019 | 58.9 | 2.5 |
| 7 | EGT/KRT | 6.9 | 501 | 57 | 5.0 | 6.4 | 847 | 90.4 | 3.0 |
| | EGT Non-carriers | | | | | | | | |
| 8 | KRT/KGT | 8.0 | 674 | 44 | 3.7 | 4.6 | 731 | 83.6 | 3.4 |
| 9 | KGT/KGT | 9.3 | 1090 | 79 | 2.3 | 9.7 | 1439 | 66.4 | 1.7 |
| 10 | KRT/KRT | 8.8 | 506 | 48 | 4.9 | 12.5 | 1306 | 50.0 | 1.9 |
| 11 | KRT/EGM | 10.5 | 595 | 53 | 4.2 | 12.1 | 1368 | 56.3 | 1.8 |
| 12 | KGT/KGM | 6.0 | 593 | 51 | 4.2 | 7.1 | 1086 | 65.4 | 2.3 |
| | Mean ± SD | 7.9 ± 1.7 | 596 ± 234 | 60 ± 11 | 4.8 ± 1.8 | 7.3 ± 3 | 1063 ± 237 | 69 ± 15 | 2.5 ± 0.5 |

Abbreviations as for Table 1.
*Denotes change from first and fifth doses.

FIG. 8

Table 4. Plasma Kinetics of DCA and Urinary Levels of DCA, Maleylacetone and Delta-Aminolevulinate in Patients with Genetic Mitochondrial Diseases.

| Patient | GSTz/MAAI genotype | Plasma | | | | | | Urine | | |
|---|---|---|---|---|---|---|---|---|---|---|
| | | Trough (µg/ml) | C max (µg/ml) | AUC (µg/ml*min) | t 1/2 (min) | CL (ml/min) | | DCA | MA | δ-ALA |
| | | | | | | | | (mmol/mol Cr) | | |
| 1 | EGT/EGT | 1.3 | 24.0 | 7800 | 124 | 3.17 | | nd | 0.6 | 2.0 |
| 2 | EGT/EGT | 0.6 | 28.0 | 8100 | 173 | 2.85 | | nd | 0.8 | 2.4 |
| 3 | EGT/KGT | 22.0 | 33.7 | 20997 | 367 | 1.19 | | 3.8 | 5.6 | 2.9 |
| 4 | EGT/KGT | 7.8 | 47.9 | 17488 | 218 | 1.43 | | 13.5 | 7.2 | 3.5 |
| 5 | KGT/EGM | 20.6 | 37.6 | 27420 | 489 | 0.91 | | nd | 1.3 | 2.1 |
| 6 | EGM/EGM | 46.0 | 50.2 | 146076 | 1816 | 0.17 | | 41.3 | 7.5 | 5.4 |

Data are from samples obtained after an oral dose of 12.5 mg/kg DCA (75% $^{13}$C/25% $^{12}$C) following 12 months of $^{12}$C-DCA administration (12.5 mg/kg/12 hours). Trough levels represent the plasma concentrations measured 12 hours after the last administration of 12.5 mg/kg $^{12}$C-DCA and immediately before administration of the $^{12}$C/$^{13}$C-DCA mixture.

Abbreviations: See Tables 1 and 2; δ-ALA, delta-aminolevulinate; nd, not detected.

FIG. 9

METHODS, ASSAYS, AND KITS RELATED TO DICHLOROACETATE (DCA)

CROSS-REFERENCE TO RELATED APPLICATIONS

This application is the 35 U.S.C. §371 national stage of PCT application PCT/US2011/040282, filed Jun. 14, 2011, which claims priority to and the benefit of U.S. Provisional Application No. 61/354,453, filed Jun. 14, 2010, both of which are hereby incorporated by reference in their entirety.

SEQUENCE LISTING

This application contains a sequence listing filed in electronic form as an ASCII.txt file entitled 222106-1575_ST25.txt, created on Mar. 30, 2017. The content of the sequence listing is incorporated herein in its entirety.

STATEMENT OF GOVERNMENTAL SUPPORT

This invention was made with government support under grant number R01 ES014617-01, awarded by the National Institutes of Health of the United States government. The government has certain rights in the invention.

BACKGROUND

The xenobiotic dichloroacetate (DCA) is ubiquitous in our biosphere as a product of water chlorination and as a metabolite of certain industrial solvents and pharmaceuticals. As such, it has generated interest among environmental scientists as a potential human health hazard. However, DCA has long been used as an investigational drug for the treatment of several acquired or congenital disorders of intermediary metabolism, particularly genetic mitochondrial diseases that have a frequency in the general population of >1 in 5,000. Interest in its therapeutic potential has recently intensified, based on reports of its selective pro-apoptotic and antiproliferative actions in human cancers and in pulmonary arterial hypertension that have led to several early-phase clinical trials. In turn, the possibility of increased long-term exposure to DCA for the treatment of both rare and common diseases has heightened attention about its pharmacokinetics, biotransformation and chronic safety in humans.

SUMMARY

Embodiments of the present disclosure provide for methods, assays, and kits for predicting dosing for subjects. In addition, embodiments of the present disclosure include methods, assays, and kits, of determining if a patient can effectively metabolize one or both of phenylalanine and tryrosine.

One exemplary method of determining a dosing regime for a subject for dichloroacetate (DCA), among others, includes: obtaining a GSTz1/MAAI haplotype of a subject, wherein the one or more haplotypes have a possible risk of adverse drug effects; using the haplotype of the subject to determine if the dosing regime should be different than the standard dosing regime for the patient; and selecting a dosing regime for the subject.

One exemplary method of selecting a subject for using a standard dosing regime of DCA, among others, includes: obtaining a GSTz1/MAAI haplotype of a subject, wherein subjects having one or more haplotypes have a possible risk of adverse drug effects; and using the haplotype of the patient to determine if the subject has a risk of adverse effects using a standard dosing regime of DCA, if the subject has a risk, then the standard regime is not given to the subject.

One exemplary method of determining if a patient can effectively metabolize one or both of phenylalanine and tryrosine, among others, includes: obtaining a GSTz1/MAAI haplotype of a subject; and using the haplotype of the subject to determine if the subject effectively metabolizes one or both of phenylalanine and tryrosine.

One exemplary array for determining a GSTz1/MAAI haplotype of a subject, among others, includes: a first target substrate that can detect the presence of KGM allele in the GSTz1/MAAI haplotype, a second target substrate that can detect the presence of the EGM allele in the GSTz1/MAAI haplotype, a third target substrate that can detect the presence of the EGT allele in the GSTz1/MAAI haplotype, a fourth target substrate that can detect the presence of the KGT allele in the GSTz1/MAAI haplotype, and a second target substrate that can detect the presence of the KRT allele in the GSTz1/MAAI haplotype.

One exemplary kit for determining a determining a dosing regime for a subject for DCA, among others, includes: an array of the present disclosure, directions for use of the array, and directions describing one or more types of GSTz1/MAAI haplotypes that have a risk of adverse drug effects if given standard dosing regime.

One exemplary kit for determining a determining if a patient can effectively metabolize one or both of phenylalanine and tryrosine, among others, includes: an array of the present disclosure, directions for use of the array, and directions describing one or more types of GSTz1/MAAI haplotypes that indicates if the subject effectively metabolizes one or both of phenylalanine and tryrosine Other compositions, methods, kits, features, and advantages of this disclosure will be or become apparent to one with skill in the art upon examination of the following drawings and detailed description. It is intended that all such additional compositions, methods, features, and advantages be included within this description, be within the scope of this disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure.

FIG. 1A illustrates the bifunctionality of GSTz1/MAAI, while

FIG. 6 illustrates Table 1 that describes the pharmacokinetics of 25 mg/kg 1, 2-$^{13}$C-DCA after 1 and 5 doses.

FIG. 7 illustrates Table 2 that describes the urinary levels of $^{12}$C-DCA and maleylacetone after 5 Days of 25 mg/kg/d DCA.

FIG. 8 illustrates Table 3 that describes the pharmacokinetics of 2.5 μg/kg of 1, 2-$^{13}$C-DCA after 1 and 5 doses.

FIG. 9 illustrates Table 4 that describes the plasma kinetics of DCA and urinary levels of DCA, maleylacetone and delta-aminolevulinate in patients with genetic mitochondrial diseases.

DETAILED DESCRIPTION

Figure 1A:
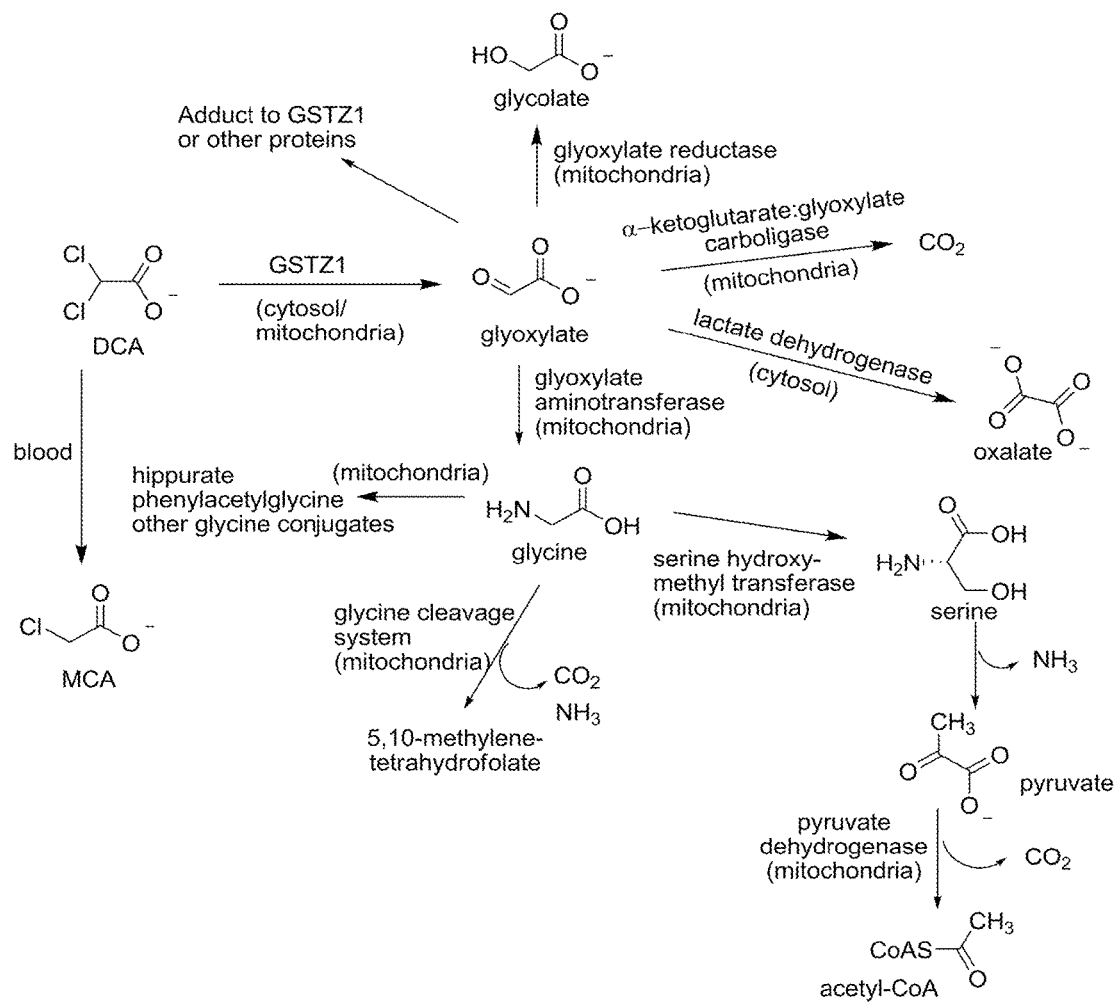

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of synthetic organic chemistry, biochemistry, biology, molecular biology, recombinant DNA techniques, pharmacology, and the like, which are within the skill of the art. Such techniques are explained fully in the literature. In particular, See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. (1985)); "Transcription and Translation" (B. D. Hames & S. J. Higgins eds. (1984)); "Animal Cell Culture" (R. I. Freshney, ed. (1986)); "Immobilized Cells and Enzymes" (IRL Press, (1986)); B. Perbal, "A Practical Guide To Molecular Cloning" (1984), each of which is incorporated herein by reference.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

Definitions

In describing and claiming the disclosed subject matter, the following terminology will be used in accordance with the definitions set forth below.

The term "array" encompasses the term "microarray" and refers to an ordered array of target substrates presented for binding to a compound such as a polypeptide, polynucleotide, or a compound, or particle that can be used to attached to a polypeptide, polynucleotide, or a compound. In an embodiment, the array includes one or more target substrates that can have an affinity for one or more types of polypeptide, polynucleotide, or a compound, or particle that can be used to attached to a polypeptide, polynucleotide, or a compound.

An "array" includes any two-dimensional or substantially two-dimensional (as well as a three-dimensional) arrangement of addressable regions including target substrates. Where the arrays are arrays of target substrates, the target substrates may be adsorbed, physisorbed, chemisorbed, and/or covalently attached to the arrays.

A substrate may carry one, two, four or more arrays disposed on a front surface of the substrate. Depending upon the use, any or all of the arrays may be the same or different from one another and each may contain multiple spots or features. A typical array may contain one or more, including more than two, more than ten, more than one hundred, more than one thousand, more ten thousand features, or even more than one hundred thousand features, in an area of less than about 20 cm$^2$ or even less than about 10 cm$^2$ (e.g., less than about 5 cm$^2$, including less than about 1 cm$^2$ or less than about 1 mm$^2$ (e.g., about 100 μm$^2$, or even smaller)). For example, features may have widths (that is, diameter, for a round spot) in the range from about 10 μm to 1.0 cm. Non-round features may have area ranges equivalent to that of circular features with the foregoing width (diameter) ranges.

Arrays can be fabricated using drop deposition from pulse-jets of target substrates. Such methods are described in detail, for example, in U.S. Pat. No. 6,242,266, U.S. Pat. No. 6,232,072, U.S. Pat. No. 6,180,351, U.S. Pat. No. 6,171,797, and U.S. Pat. No. 6,323,043, which are incorporated herein by reference.

An array "package" may be the array plus a substrate on which the array is deposited, although the package may include other features (such as a housing with a chamber). A "chamber" references an enclosed volume (although a chamber may be accessible through one or more ports). It will also be appreciated that throughout the present application, that words such as "top," "upper," and 'lower" are used in a relative sense only.

An array is "addressable" when it has multiple regions of different moieties (e.g., different target substrates) such that a region (i.e., a "feature" or "spot" of the array) at a particular predetermined location (i.e., an "address") on the array will detect a particular target. Array features are typically, but need not be, separated by intervening spaces.

A "scan region" refers to a contiguous (preferably, rectangular) area in which the array spots or features of interest, as defined above, are found or detected. The scan region is that portion of the total area queried from which resulting signal is detected and recorded.

An "array layout" refers to one or more characteristics of the features, such as feature positioning on the substrate, one or more feature dimensions, and an indication of a moiety at a given location.

Use of the term "affinity" can include biological interactions and/or chemical interactions between or among a target substrate (e.g., a compound or bio-molecule (e.g., polypeptide or polynucleotide)) and a target of interest (e.g., an allele). The biological interactions can include, but are not limited to, bonding or hybridization among one or more biological functional groups of the target substrate or target. The chemical interaction can include, but is not limited to, bonding among one or more functional groups (e.g., organic and/or inorganic functional groups) located on the target.

The term "unit dosage form," as used herein, refers to physically discrete units suitable as unitary dosages for human and/or animal subjects, each unit containing a predetermined quantity of a compound (e.g., DCA) calculated in an amount sufficient (e.g., presence of one or more alleles, weight of host, disease, severity of the disease, and the like) to produce the desired effect in association with a pharmaceutically acceptable diluent, carrier or vehicle while also reducing the risk of acetaminophen-induced liver toxicity. The specifications for unit dosage forms depend on the particular compound employed, the route and frequency of administration, and the effect to be achieved, and the pharmacodynamics associated with each compound in the host.

The terms "effective amount" or "effective dose" as used herein refers to that amount of an embodiment of the present disclosure being administered to treat or prophylactically treat the subject (e.g., reduce risks associated with a standard DCA regime).

As used herein, "treat", "treatment", "treating", and the like refer to acting the condition or disease. The improvement or alteration may include an improvement in symptoms or an alteration in the physiologic pathways associated with the condition or disease. "Treatment," as used herein, covers one or more treatments of a disease or condition in a subject (e.g., a mammal, typically a human or non-human animal of veterinary interest).

As used herein, the terms "prophylactically treat" or "prophylactically treating" refers completely or partially preventing (e.g., about 50% or more, about 60% or more, about 70% or more, about 80% or more, about 90% or more, about 95% or more, or about 99% or more) the condition or disease.

The term "therapeutically effective amount" as used herein refers to that amount of an embodiment of the composition or pharmaceutical formulation being administered that will relieve to some extent one or more of the symptoms of the condition or disease being treated, and/or that amount that will prevent, to some extent, one or more of the symptoms that the subject being treated has or is at risk of developing.

By "administration" is meant introducing a composition (DCA) to a subject. Administration can include routes, such as, but not limited to, intravenous, oral, topical, subcutaneous, intraperitoneal, intraarterial, inhalation, vaginal, rectal, nasal, introduction into the cerebrospinal fluid, or instillation into body compartments can be used. A preferred route is oral administration.

As used herein, the term "subject" includes humans, mammals (e.g., cats, dogs, horses, etc.), and other living animals. In particular, the host is a human subject. Typical subjects to which embodiments of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like.

Discussion:

Embodiments of the present disclosure provide for methods, assays, and kits for predicting dosing for subjects. Embodiments of the present disclosure use haplotypes of GSTZ1 gene to determine fast and slow metabolizers of dichloroacetate (DCA), which can be used to improve rational dosing of DCA and prevent or reduce toxicity when using DCA. Embodiments of the present disclosure enable pharmacogenetic testing for DCA and/or molecular diagnostics kits for treatment of subjects considering efficacy and toxicity of DCA during treatment. In an embodiment, the method includes determining if a subject has certain alleles. If so, the dosing level of the subject should be altered and/or monitored for adverse drug effects. In addition, embodiments of the present disclosure include methods of determining if a patient can effectively metabolize one or both of phenylalanine and tryrosine and assays and kits for determining if a patient can effectively metabolize one or both of phenylalanine and tryrosine.

The investigational drug DCA is dehalogenated to glyoxylate by the zeta-1 family isoform of glutathione transferase (GSTz1). This enzyme is identical to maleylacetoacetate isomerase (MAAI), the penultimate enzyme of the phenylalanine/tyrosine catabolic pathway. It has been determined that polymorphisms in the GSTz1/MAAI gene (GSTZ1 SNPs: rs7975 (g.5696G>A, Glu32Lys), rs7972 (g.5726G>A, Gly42Arg), and rs1046428 (g.6772C>T, Thr82Met) modify the kinetics of DCA and, consequently, the risk of adverse effects from the drug. GSTz1/MAAI haplotype clearly segregated subjects into fast and slow DCA metabolizers. Those who metabolized DCA slowly showed markedly delayed plasma clearance, increased excretion of unmetaboized drug and increased urinary accumulation of potentially toxic tyrosine metabolites (e.g., risks, additional details provided in the Example). Thus, GSTz1/MAAI haplotype predicts the toxicogenetics of DCA. This information can be used prospectively to adjust drug dosing and mitigate risk of adverse events when using DCA. In an embodiment, the GSTz1/MAAI haplotype can include one or two of the following: a KGM allele, a EGM allele, a EGT allele, a KGT allele, and a KRT allele. Additional details are provided in the Examples.

Methods, assays, and kits using the GSTz1/MAAI genotype can be used to predict the toxicokinetics of DCA in a subject (e.g., human or other mammal). Knowledge of GSTz1/MAAI genotype can be used to determine if the subject is at a heightened risk (or a slow metabolizer of DCA) for developing adverse drug effects to DCA. Once an individual is known to include certain alleles, dose adjustments can be made so that the individual can tolerate the DCA. The methods, assays, and kits of the present disclosure can be use assist in those individuals enrolled in clinical trials of DCA for treatment of mitochondrial diseases, cancer or other conditions. Based on this information and the information described in Example 1 and 2, kits, assays, and methods can be designed to predict who should use DCA and/or that adjustments should be made to dosing levels.

As mentioned above, an embodiment of the present disclosure provides for a method of determining a dosing regime for a patient for DCA. The method includes obtaining a GSTz1/MAAI haplotype of a subject (e.g., a human patient), using the haplotype of the subject to determine if the dosing regime should be different than the standard dosing regime for the patient, and selecting a new dosing regime for the subject. In an embodiment, a subject having at least one KGM allele in the GSTz1/MAAI haplotype should have the standard dosing regime reduced. In an embodiment, a subject having at least one EGM allele in the GSTz1/MAAI haplotype should have the standard dosing regime reduced. In an embodiment, a subject not having at least one EGT allele in the GSTz1/MAAI haplotype should have the standard dosing regime reduced. In an embodiment, a subject having KRT allele homozygosity in the GSTz1/MAAI haplotype should have the standard dosing regime reduced.

In general, a patient is given a standard dosing regime (e.g., daily dosage of DCA, frequency of administration, and the like) based on age, size, health, and the like, but as noted herein, the standard dosing regime is not appropriate for some subjects having certain GSTz1/MAAI haplotypes (e.g., slow metabolizers of DCA). In an embodiment, the standard dosing applies to subjects having haplotype of EGT/EGT or any EGT heterozygote. In general, the standard dosing regime for a healthy adult is about 5 to 25 mg/kg/day and the standard dosing regime for a healthy child is about 10 to 50 mg/kg/day. In an embodiment, the amount of the reduction of the standard dosing regime for a subject (a healthy adult or child) that is a slow DCA metabolizer (e.g., having one of allele identified herein) should be about 10% or more, about 20% or more, about 30% or more, about 40% or more, about 50% or more, about 60% or more, about 70% or more, or about 80% or more. In an embodiment, the amount of the reduction can initially be small and increased based on the response of the subject.

An embodiment of the present disclosure includes selecting a subject (e.g., human patient) for using a standard dosing regime of DCA. The method includes obtaining a GSTz1/MAAI haplotype of a subject and using the haplotype of the subject to determine if the subject has a risk of adverse effects using a standard dosing regime of DCA. If the patient has a risk, then the standard regime is not given to the subject. If the patient does not have a risk, then the standard regime can be given to the subject. Thus, the subject is given a dosing regime based on the haplotype of the patient. In an embodiment, a patient has a risk if the patient has at least one KGM allele in the GSTz1/MAAI haplotype. In an embodiment, a patient has a risk if the patient has at least one EGM allele in the GSTz1/MAAI haplotype. In an embodiment, a patient has a risk if the patient does not have at least one EGT allele in the GSTz1/MAAI haplotype. In an embodiment, a patient has a risk if the patient has KRT allele homozygosity.

An embodiment of the present disclosure includes an array (e.g., an addressable array) for determining a GSTz1/MAAI haplotype of a patient. The array includes a substrate including a target substrate having an affinity for a specific allele of the GSTz1/MAAI haplotype. In an embodiment, the array includes a targeting substrate having an affinity for one or more of the following: a KGM allele, a EGM allele, a EGT allele, a KGT allele, and a KRT allele. Thus the array has the ability to be used to detect the presence of one or more of the alleles of the GSTz1/MAAI haplotype. In an embodiment, the genotyping testing can be performed on a new custom-designed DNA chip that calls or differentiate alleles labeled with two different fluorescent dyes (e.g., Cy-3 or Cy-5 or Vic and Fam), or these polymorphisms can be added to the existing DNA chips currently approved by FDA and used in diagnostic labs from OSMETHEC Molecular Diagnostics and Illumina ADME drug metabolizing chip.

An embodiment of the present disclosure includes a kit for determining a dosing regime for a patient for DCA. The kit can include an array, such as one described herein, directions for use of the array, and directions describing one or more types of GSTz1/MAAI haplotypes that have a risk of adverse drug effects if given a standard dosing regime, and optionally a test container, a sampling system. The GSTz1/MAAI haplotypes having a risk of adverse drug effects are described herein. In addition, the kit can include an alternative dosing regime for patients who may have a risk of adverse drug effects.

As mentioned above, an embodiment of the present disclosure includes determining if a patient can effectively metabolize one or both of phenylalanine and tryrosine. The method includes obtaining a GSTz1/MAAI haplotype of a patient and using the haplotype of the patient to determine if the patient effectively metabolizes one or both of phenylalanine and tryrosine. If the patient has a risk of not effectively metabolizing one or both of phenylalanine and tryrosine, appropriate changes to diet and/or administration of a drug (e.g., DCA) can be made to avoid the adverse effects. In an embodiment, a patient has a risk if the patient has at least one KGM allele in the GSTz1/MAAI haplotype. In an embodiment, a patient has a risk if the patient has at least one EGM allele in the GSTz1/MAAI haplotype. In an embodiment, a patient has a risk if the patient has does not have an EGT allele.

An embodiment of the present disclosure includes a kit for determining if a patient can effectively metabolize one or both of phenylalanine and tryrosine. The kit can include an array, such as one described herein, directions for use of the array, and directions describing one or more types of GSTz1/MAAI haplotypes that can or cannot effectively metabolize one or both of phenylalanine and tryrosine, and optionally a test container, a sampling system. The GSTz1/MAAI haplotypes that indicate if a subject can or cannot effectively metabolize one or both of phenylalanine and tryrosine, are described herein.

Now having described the embodiments of the present disclosure, in general, the following Examples describe some additional embodiments of the present disclosure. While embodiments of present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Brief Introduction

Dichloroacetate (DCA), a chemical relevant to environmental science and allopathic medicine, is dehalogenated by the bifunctional enzyme glutathione transferase zeta (GSTz1)/maleylacetoacetate isomerase (MAAI), the penultimate enzyme in the phenylalanine/tyrosine catabolic pathway. We postulated that polymorphisms in GSTz1/MAAI modify the toxicokinetics of DCA. GSTz1/MAAI haplotype significantly affected the kinetics and biotransformation of 1, 2-$^{13}$C-DCA when it was administered at either environmentally (μg/kg/d) or clinically (mg/kg/d) relevant doses. GSTz1/MAAI haplotype also influenced the urinary accumulation of potentially toxic tyrosine metabolites. Atomic modeling revealed that GSTz1/MAAI variants associated with the slowest rates of DCA metabolism induced structural changes in the enzyme homodimer predicting protein instability or abnormal protein-protein interactions. Knowledge of GSTz1/MAAI haplotype can be used prospectively to identify individuals at potential risk of DCA's adverse side effects from environmental or clinical exposure or who may exhibit aberrant amino acid metabolism in response to dietary protein.

Introduction:

The xenobiotic dichloroacetate (DCA) is ubiquitous in our biosphere as a product of water chlorination and as a metabolite of certain industrial solvents and pharmaceuticals[1]. As such, it has generated interest among environmental scientists as a potential human health hazard. However, DCA has long been used as an investigational drug for the treatment of several acquired or congenital disorders of intermediary metabolism, particularly genetic mitochondrial diseases[2,3] that have a frequency in the general population of >1 in 5,000[4]. Interest in its therapeutic potential has recently intensified, based on reports of its selective pro-apoptotic and antiproliferative actions in human cancers[5-15] and in pulmonary arterial hypertension[16-19] that have led to several early-phase clinical trials[20-27]. In turn, the possibility of increased long-term exposure to DCA for the treatment of both rare and common diseases has heightened attention about its pharmacokinetics, biotransformation and chronic safety in humans.

Figure 1B:
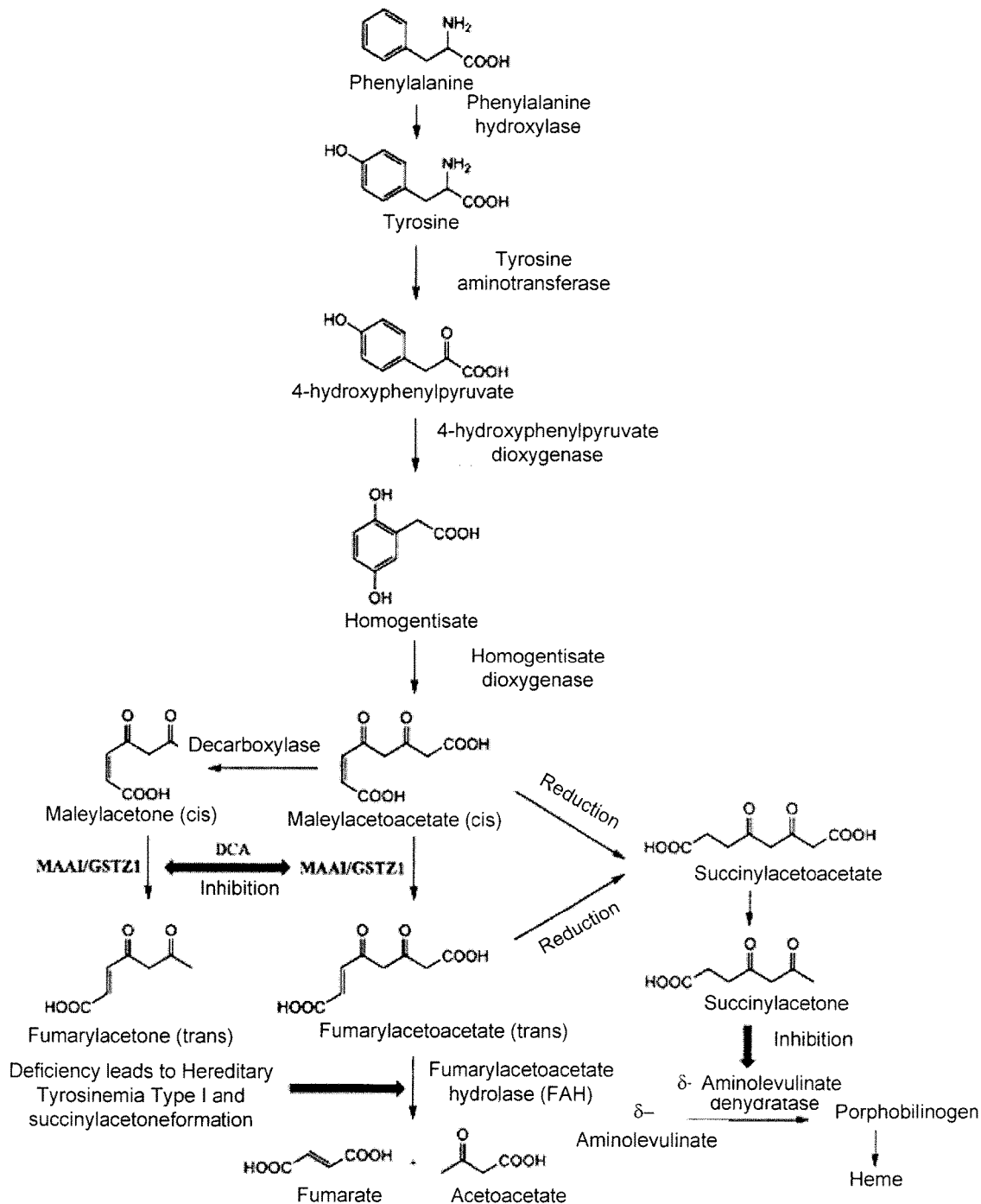
FIG. 1B illustrates the tyrosine catabolic pathway as a function of MAAI.

DCA is dehalogenated to glyoxalate, a naturally occurring compound in mammals, by the zeta-1 family isoform of cytosolic glutathione transferase (GSTz1)[28]. GSTz1 is identical to maleylacetoacetate isomerase (MAAI), the penultimate enzyme of the phenylalanine/tyrosine catabolic pathway[29] (FIGS. 1A and 1B). DCA inhibits GSTz1/MAAI[14], which leads to a marked decrease in its plasma clearance[1,30]. Enzyme inhibition by DCA also results in the accumulation of the potentially hepatotoxic tyrosine intermediates maleylacetoacetate and maleylacetone[31] and of delta-aminolevulinate, a precursor of heme synthesis that has been associated with neurotoxic effects, including peripheral neuropathy[29]. Reversible increases in serum transaminases and reversible peripheral neuropathy have been reported in association with chronic DCA exposure[1,32]. Although the plasma clearance of DCA has been demonstrated in rats and humans to be inversely related to age[33], there remains marked variability in both the clinical pharmacokinetics and toxicity of the drug that cannot be explained by age alone.

The human GSTz1/MAAI gene is located on chromosome 14q24.3. Three non-synonymous single nucleotide polymorphisms (SNPs) have been reported for GSTz1/MAAI that show different activity towards DCA and certain other xenobiotic haloacids[34]. The allele and haplotype frequencies for the known SNPs are known to vary among racial and ethnic groups[2]. In vitro studies using purified proteins corresponding to the four haplotypes revealed the rare KRT haplotype to have 10-fold higher Km and Vmax values for DCA and glutathione compared to the other haplotypes. This finding suggested that humans who possess the KRT variant might exhibit a markedly different pharmacokinetic and toxicological profile to DCA than would subjects who possessed the more common haplotypes. We tested this hypothesis by determining the relative effect of GSTz1/MAAI haplotype on the kinetics of DCA and on tyrosine metabolism in healthy adults exposed to short-term administration of DCA at both environmental and clinically relevant concentrations. We compared these findings to those obtained from patients with genetic mitochondrial diseases who participated in a clinical trial of chronic DCA treatment.

Methods:

Materials: Crystalline sodium 1, 2 $^{13}$C-DCA (99% pure) was custom synthesized (Cambridge Isotope Laboratories, Cambridge, Mass.). Crystalline sodium $^{12}$C-DCA (99% pure) was purchased from TCI America, Portland, Oreg. Other chemicals and materials were obtained from previously reported sources[30].

Clinical Studies. All studies were approved by the Institutional Review Board of the University of Florida and were conducted in the Clinical Research Unit (CRU) in Shands Hospital at UF. Informed consent was obtained from all subjects prior to their enrollment. We enrolled 588 healthy adults into a screening database to identify individuals with various GSTz1/MAAI haplotypes. Twelve individuals (5 males), aged 21 to 37 years, were consented to undergo detailed pharmacokinetic evaluation of DCA, based on GSTz1/MAAI haplotype. Subjects received a weight-maintaining diet that was prepared by the bionutrition staff of the CRU, using distilled water for food preparation and drinking, to minimize daily fluctuations in environmental intake of DCA. Diets began 4 days before each kinetic investigation and continued until completion of blood and urine collections. Oral DCA (2.5 µg/kg) was administered daily after an overnight fast for 5 consecutive days to reflect a dose similar to that obtained from consumption of chlorinated municipal drinking water[35]. The plasma kinetics of 1, 2 and $^{13}$C-DCA was determined on the first and fifth day of drug administration. $^{12}$C-DCA was administered on days 2-4. After at least a 30-day washout, the same subjects received oral DCA for 5 days at a dose of 25 mg/kg/d to reflect a typical exposure level of the compound when administered as a therapeutic agent to patients[3,32]. Blood was withdrawn from an antecubital vein on each day of $^{13}$C-DCA administration at −10, 0, 5, 10, 20 and 30 minutes and at 1, 2, 3, 4, 6, 8, 12 and 24 hours and placed into heparinized Vacutainer tubes from which the stopper had been removed. Urine was collected at 24 hours during each kinetic investigation. Blood samples and urine were processed as previously described[30,36].

Analytical Methods: Plasma concentrations of DCA and tyrosine and urinary levels of maleylacetone were measured by gas chromatography-mass spectrometry (Agilent Technologies, Model 5973C, Santa Clara, Calif.)[37]. Urinary delta-aminolevulivate was quantified by liquid chromatography-mass spectrometry (Thermo Scientific, Model TSQ 7000, San Jose, Calif.)[38]. Breath samples were collected by direct exhalation using a common straw into 10 ml Exetainer tubes (Labco, Ltd). The amount of $^{13}CO_2$ in the Exetainer breath storage tubes was measured[39] with a Europa Scientific 20/20 gas isotope ratio mass spectrometer (Europa Scientific, Cincinnati, Ohio).

Pharmacokinetic Analysis: The plasma-concentration time curve for all DCA measurements were fitted into a noncompartmental pharmacokinetic model for each patient using WinNonLin, version 5.01 software (Pharsight, Mountain View, Calif.), obtained through the academic license program. We determined the maximum plasma concentration of DCA ($C_{max}$) and the time to achieve $C_{max}$ ($T_{max}$). Through the WinNonLin software, we calculated the area under the plasma concentration-time curve from time 0 to 1440 min (24 hr) for DCA ($AUC_{0-1440\ min}$) using the linear-trapezoidal method. At least three sampling points were used by the modeling software to estimate the first order elimination rate constant (λz) for each time-concentration curve. The software calculated the terminal phase elimination half-life ($t_{1/2}$) as ln (2)/λz and the total body clearance (CL) of DCA as the dose/AUC ($_{0-1440\ min}$).

DNA Isolation, Genotyping and Haplotype Analysis: DNA was isolated from mouth wash, blood and plasma samples from 588 healthy adults, comprised of 200 (34%) males and 388 (66%) females. Of this population, 355 (60%) were Caucasian, 96 (17%) were black, 83 (14%) were Asian and 54 (9%) were Hispanic. They were aged 20 to 55 years, and 6 children aged 2 to 10 years, with congenital lactic acidosis. DNA was isolated using Qiagen Gentra Puregene Buccal Cell and blood Kits (Qiagen Inc., CA, USA).

DNA samples were genotyped for 3 non-synonymous SNPs: G94>A (rs3177427) Glu→Lys at position 32; G124>A (rs7972) Gly→Arg at position 42; and C245>T (rs1046428) Thr→Met at position 82) in the GSTz1/MAAI gene by pyrosequencing[2]. Haplotypes were inferred by computational methods using the Bayesian haplotype reconstruction program, PHASE version 2.1[40].

Resequencing and Mutation Discovery: A DNA sample from a subject with the KGM/KGT haplotype who showed the lowest DCA metabolism among subjects was selected for further analysis by resequencing and mutation discovery. The exons and intron/exon boundaries, 5' and 3' untranslated regions (UTR) of GSTZ1/MAAI gene were amplified by PCR and the purified PCR products were evaluated by direct sequencing using the Amersham Biosciences ET-terminator chemistry method. Bidirectional DNA sequence data were compiled and polymorphic sites were identified using PolyPhred[41]. After identifying the novel Val 99 Met mutation in this subject, DNA samples from individuals who showed fast or slow DCA metabolism were also resequenced to determine whether they carried this mutation.

Structural analysis: PDB code 1FW1 was displayed in PyMol. Atomic homology models were generated by substituting amino acids in the GSTz1/MAAI sequence at positions 32 (Lys→Glu), 42 (Gly→Arg), 82 (Thr→Met) and 99 (Val→Met). This sequence was used for generation of an atomic homology model using SWISS-Mod in the automated mode. FIG. 5 was made with PyMol.

Statistical Analyses: We determined the mean, S.D. and statistical significance of the data using Excel software (Microsoft, Redmond, Wash.). A two-sided Student's t test was used to analyze kinetic and metabolic data between groups and, in all cases, a p value of ≤0.05 was considered to be statistically significant.

Figure 2:
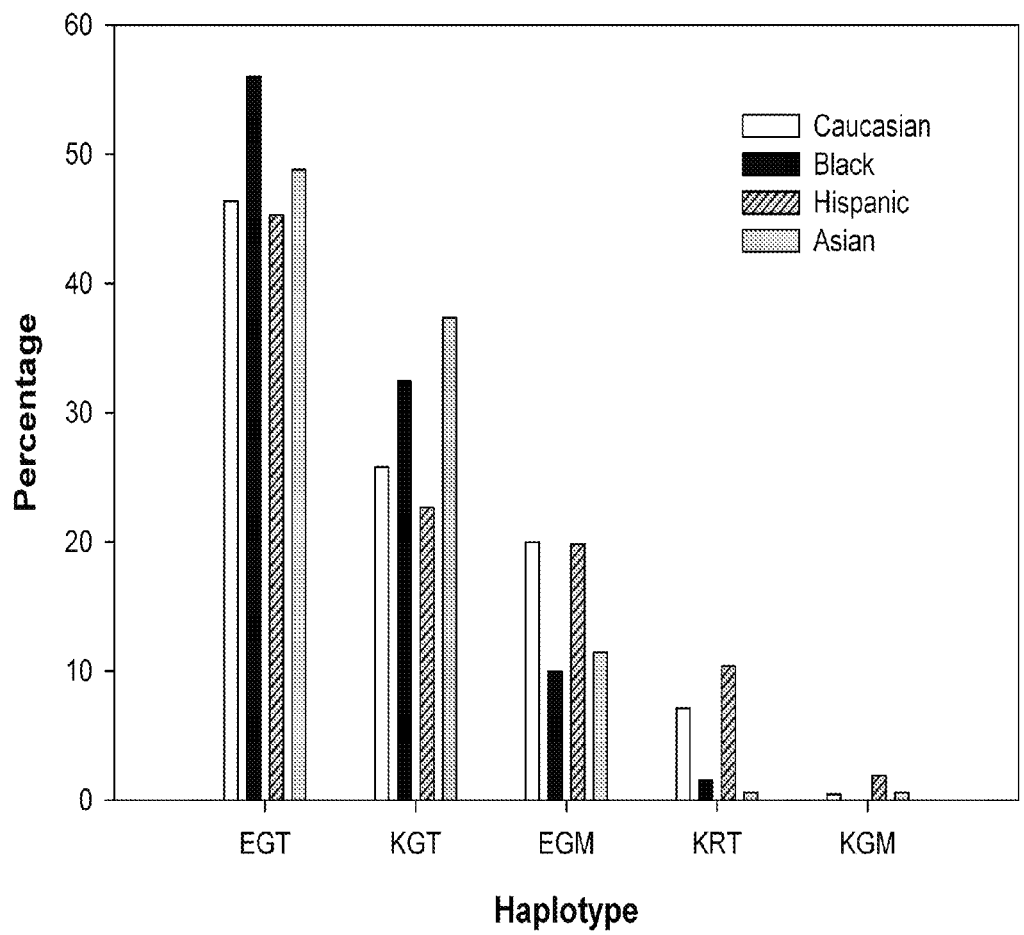
FIG. 2 illustrates the GSTz1/MAAI Haplotype Frequencies in 588 Subjects.

Results:

FIG. 2 shows the GSTz1/MAAI haplotype frequencies among 588 healthy subjects comprising this study. The four most common haplotypes (EGT, KGT, EGM and KRT) showed a distribution consistent with those previously reported across racial and ethnic populations[2]. The frequency of the wildtype (EGT) haplotype was similar among racial and ethnic groups: 46% in Caucasians, 56% in blacks, 45% in Hispanics and 49% in Asians, respectively (chi-square test p value=0.34). A novel KGM haplotype was detected in 5 individuals (0.4%).

Figure 3:
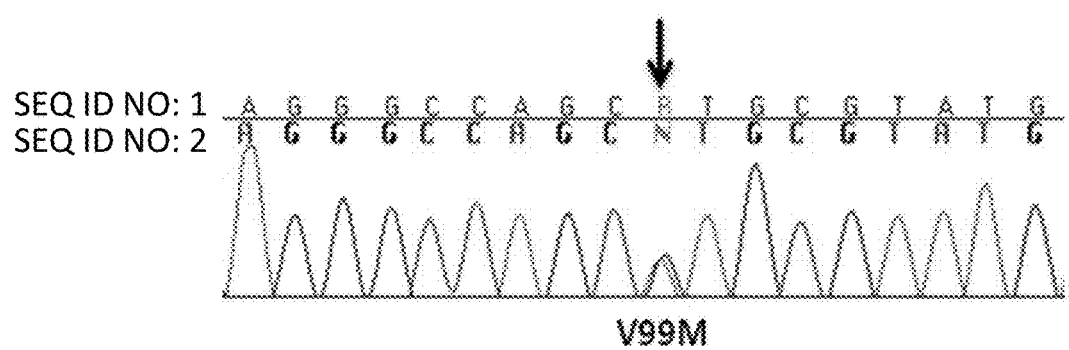
FIG. 3 illustrates the sequence chromatogram of mutation G259A (NM_145870) in exon five of GSTz1/MAAI.

Resequencing of the GSTZ1/MAAI gene in the subject with unusually low DCA metabolism resulted in identification of four novel SNPs that are not reported in the NCBI dbSNP database. A G>A missense mutation (non-synonymous SNP) at Contig position 58794086 results in substitution of (Val99Met) Val(GTG) to Met(ATG) in GSTz1/MAAI exon 5 (transcript variant 1). Amino acid Val99 is conserved in the following species; *Homo sapiens, Canis lupus familiaris, Bos taurus, Mus musculus, Gallus gallus* and *Danio rerio* (http://www.ncbi.nlm.nih.gov/sites/entrez). The 3 other SNPs were located in intronic regions: a C>T transition at Contig position 58787368, and two G>T transversions at Contig positions 58795801 and 58797488. FIG. 3 shows the sequence chromatogram of mutation (NM_145870:c.259G>A) in exon five of GSTz1/MAAI (transcript variant 1).

Figure 4A:
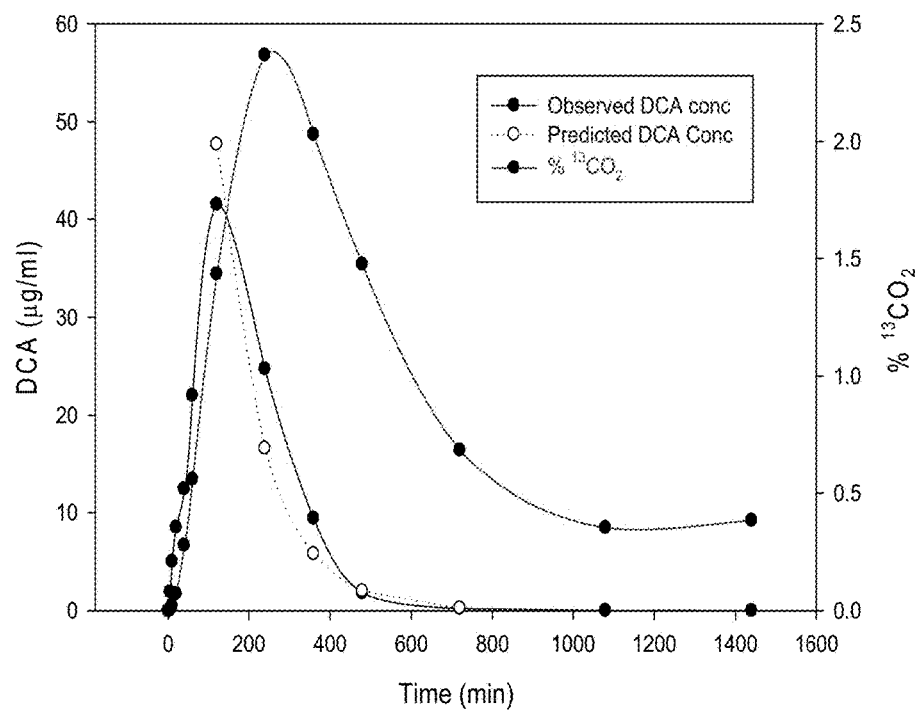
FIG. 4 illustrates the plasma kinetics and biotransformation of DCA (25 mg/kg/d). All panels show plasma $^{13}$C-DCA concentrations over 24 hours following 1 and 5 days, respectively, of oral administration of 25 mg/kg dose of 1,2-$^{13}$C-DCA. Also shown is the time course of $^{13}CO_2$ accumulation in exhaled breath as a percentage of the administered dose $^{13}$C-DCA. Panels A and B show representative data from subject 1 (EGT/EGT) in Table 1, a fast metabolizer of DCA. Panels C and D show data from subject 12 (KGM/KGT), a slow metabolizer of DCA.
Figure 4B:
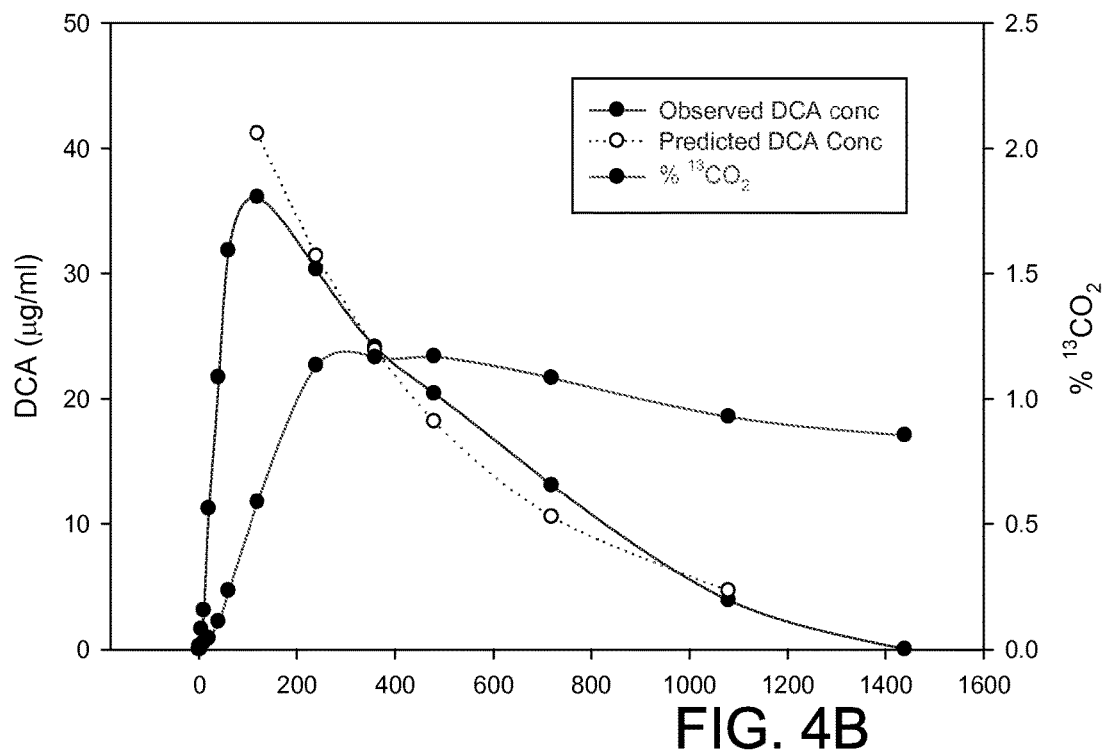

To investigate whether haplotype was a major determinant of DCA kinetics, we focused recruitment on individuals with different GSTz1/MAAI haplotypes. As shown in Table 1, GSTz1/MAAI haplotype had major effects on how subjects responded to repeated exposure to 25 mg/kg/d of DCA on the basis of plasma elimination half-life (t½), area under the concentration curve (AUC) and clearance (CL). The most rapid plasma clearance after 5 consecutive days of DCA administration was observed in subjects who harbored at least one wildtype (EGT) allele. The mean±SD plasma clearance of the first dose of DCA was similar between the 7 subjects who carried at least one EGT allele and the 5 subjects who did not (10.7±6.9 ml/min versus 7.1±6.9 ml/min; P=0.36). However, clearance after the fifth drug dose was 3-fold greater in EGT carriers than in non-carriers (2.2±0.7 ml/min versus 0.73±0.84 ml/min; P=0.01) and was highest in subjects who were homozygous for the wildtype EGT allele (Table 1 and FIGS. 4A and B). The fraction of $^{13}$C-DCA biotransformed in 24 hours to $^{13}CO_2$ after the first and fifth drug doses was identical in the EGT carriers (24±4% vs. 24±2%). In contrast, biotransformation to $^{13}CO_2$ decreased after the fifth dose in the other subjects (21.2±3% vs. 12±8%; p=0.013) resulting in a marked separation between subjects who harbored the wildtype allele and those who did not in the fraction of $^{13}CO_2$ formed within 24 hours after the fifth DCA dose (24±2% vs. 12±8%; p=0.01).

Figure 4C:
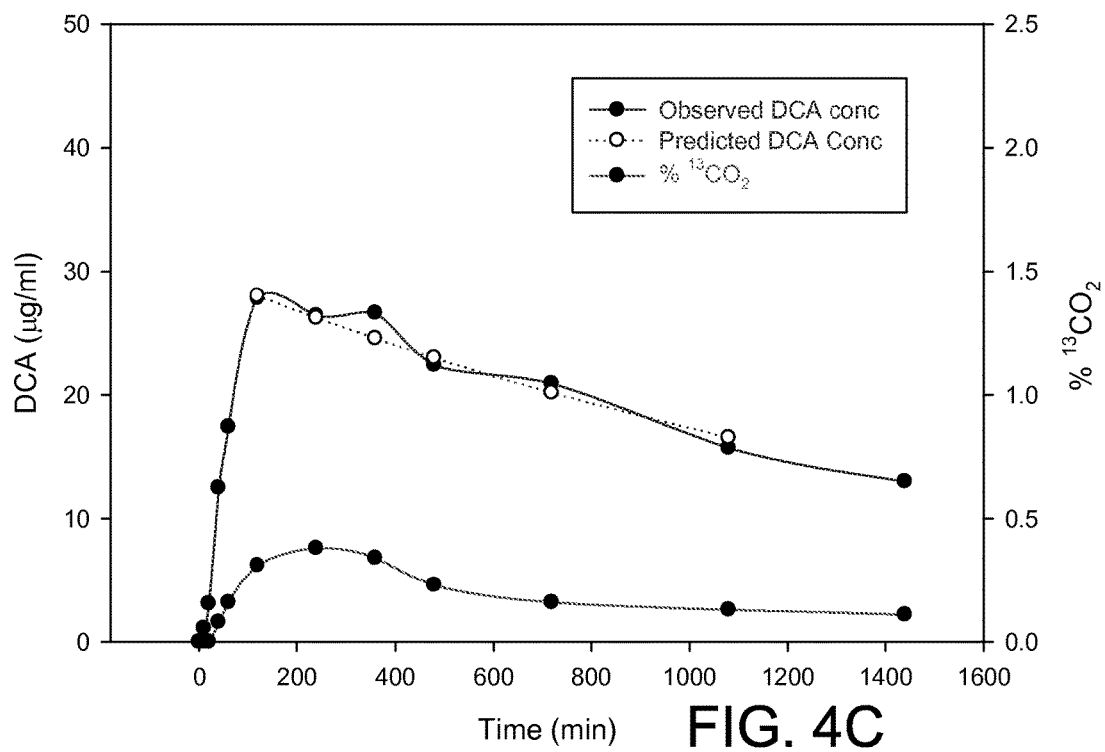
Figure 4D:
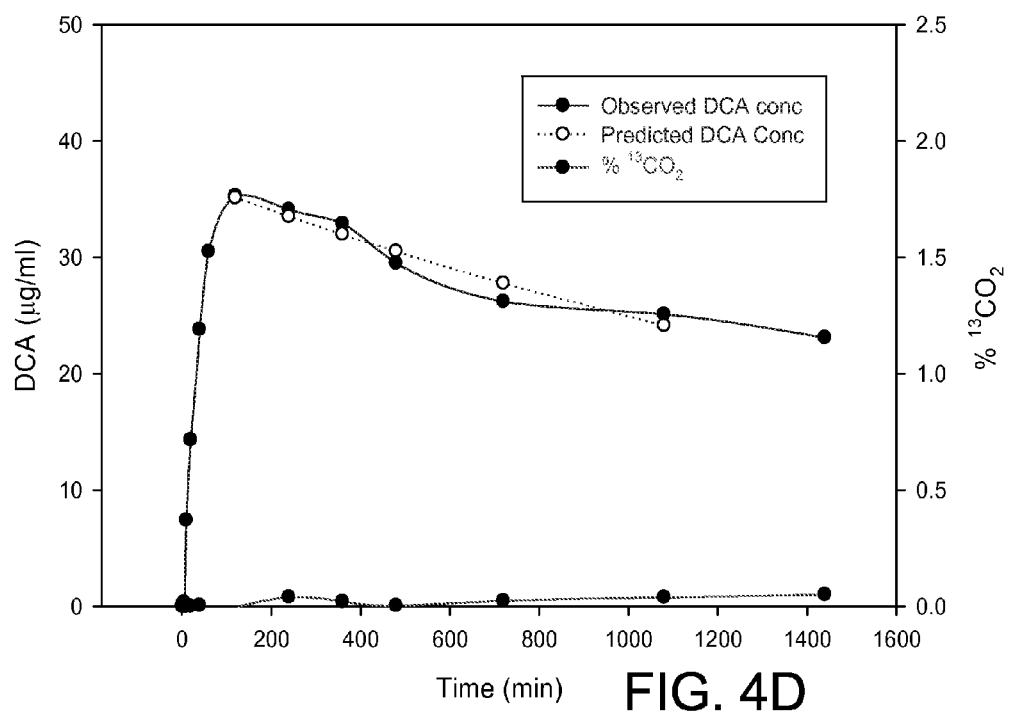

The most striking changes in DCA kinetics were found in subject 12, who possessed the rare KGM haplotype with the novel Val99Met SNP. Plasma clearance was greatly prolonged in this individual even after the first drug dose and was almost absent during the first 24 hours following the fifth dose (Table 1 and FIGS. 4C and D). Consequently, conversion of $^{13}$C-DCA to $^{13}CO_2$ after the fifth dose was lowest (2.2%) in this subject.

There was a strong association between plasma clearance of DCA and the urinary concentration of both DCA and maleylacetone, a substrate for the MAAI-catalyzed reaction. Whereas no detectable urinary $^{13}$C-DCA or maleylacetone was found in any EGT carrier, both accumulated in the urine of 4 of the 5 other subjects after 5 days of drug administration (Table 2).

We also determined the impact of 5 days of environmental DCA exposure on its kinetics and biotransformation in the same subjects (Table 3). Repeated DCA administration led to a 1.8-fold increase in AUC (596±234 ng/ml/min vs. 1063±237 ng/ml/min; p<0.01) and to a 2-fold decrease in Cl (4.8±1.8 ml/min vs. 2.5±0.5 ml/min; p<0.01). Subjects with the EGT allele cleared the fifth DCA dose 17% more rapidly as did subjects who did not possess this allele (2.6±0.4 ml/min vs. 2.2±0.7 ml/min; p=0.31). The percentage of $^{13}$C-DCA biotransformed to $^{13}CO_2$ was similar between the first (15.6±4.9%) and the fifth (12.5±3.3%) doses. There was no obvious effect of GSTz1/MAAI haplotype on the biotransformation of a 2.5 μg/kg/d dose of DCA to $CO_2$.

Because of these new findings in healthy subjects between GSTz1/MAAI genotype and DCA metabolism, we genotyped 6 children (3 males) with genetic causes of mitochondrial diseases who had participated in a randomized clinical trial of DCA administered orally at a dose of 12.5 mg/kg/12 hours[3]. Patients ranged in age from 2 to 10 years at the time DCA administration commenced. Their diagnoses were pyruvate dehydrogenase deficiency (3 subjects) or one or more defects in a respiratory chain enzyme (3 subjects). We reexamined the kinetic data from these individuals that was obtained after they had received 12 continuous months of DCA and found that, as for the healthy adults, the kinetic parameters for DCA in the patients segregated according to haplotype (Table 4). Moreover, patient 6, who is homozygous for the EGM haplotype, had the slowest clearance and the highest urinary excretion of unmetabolized $^{13}$C-DCA and of maleylacetone and delta-aminolevulinate. Indeed, the urinary concentration of maleylacetone in these children chronically exposed to DCA are similar to the levels that we have measured in the urine of 19 children with untreated tyrosinemia type 1 of (5.8±6.1 mmol/mol creatinine; range: <1.0-27 mmol/mol creatinine). In contrast, urinary delta-aminolevulinate levels in DCA-treated patients were much lower than those found in tyrosinemic subjects (44±21 mmol/mol creatinine; range: 20-94 mmol/mol creatinine).

Figure 5A:
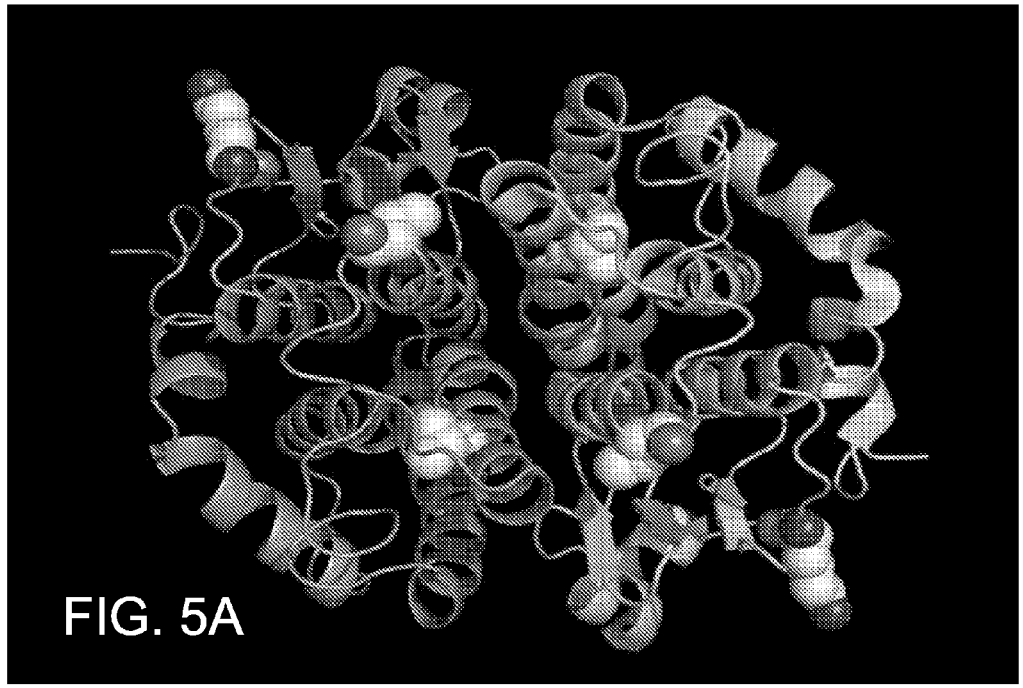
FIG. 5 illustrates the structural variance in GSTz1/MAAI. Panel A shows homodimeric GSTz1/MAAI as a ribbon diagram. Polymorphic side chains are depicted as spheres for carbon, nitrogen and oxygen. Panel B shows the crystal structure of GSTz1/MAAI and model containing the Val 99 Met mutation. GSTz1/MAAI is represented as a ribbon diagram. Covalent bonds of side chains in close proximity to position 99 (within 4 Å) of GSTz1/MAAI are shown as sticks as in 4A. The Met 99 residue is colored magenta for carbon and yellow for sulfur.

Structural Consequences of Polymorphism in GSTz1/MAAI: To determine the potential effects of polymorphisms on GSTz1/MAAI enzymatic function and DCA clearance, we mapped the polymorphic positions on the solved crystal structure, PDB code 1Fw1[42,43]. As shown in FIG. 5A, polymorphic residues associated differential metabolism of DCA are located at positions in the crystal structure that suggest multiple potential effects on GSTz1/MAAI enzymatic activity. The novel variant discovered in this study, position 99, the site of the Val99Met polymorphism, is located in an alpha helical bundle in which the side chain is completely buried. Unlike previously described variants of GSTz1/MAAI, position 99 is not exposed to solvent. Based on the crystal structure, positions 32 (Lys→Glu), 42 (Gly→Arg) and 82 (Thr→Met) are located on the solvent accessible surface.

Figure 5B:
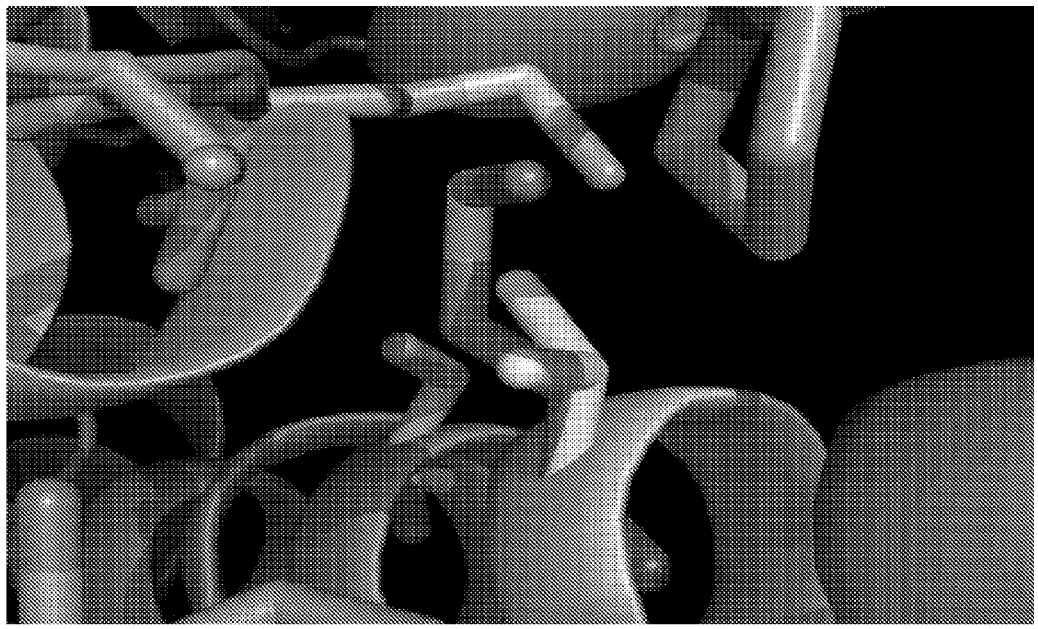

To gain insight into the specific structural consequences of expression of the GSTz1/MAAI variants, we generated atomic models of the protein in which each polymorphic position was represented by side chains expressed in individuals who exhibited different rates of DCA clearance. As shown in FIG. 5B, the Val99Met substitution, associated with the slowest rate of DCA clearance, results in steric hindrance due to the bulky nature of the Met residue compared to Val. Based on the atomic model, this buried bulky side chain is expected to form repulsive contacts with buried side chains at residues 89, 90, 103, 155, 160 and 161. In contrast, the Lys32Glu, Gly42Arg and Thr82Met side chains are located at the solvent accessible surface of GSTz1/MAAI. It is noteworthy that the surface residue Thr82Met substitution results in an alteration that is likely to affect protein stability. This effect may be due to alteration of intramolecular contacts with GSTz1/MAAI residues 65, 78 and 83 because Met cannot form hydrogen bonds with side chains at these positions. It is also notable that the Lys32Glu substitution results in an oppositely charged side chain oriented towards solvent, suggesting potential effects on protein-protein interactions. Variation at position 42 is also expected to alter the surface charge by changing the nature of the side chain from neutral to positive.

Discussion:

DCA retards its own metabolism at both environmental and clinical exposure levels by reversibly inhibiting the activity and expression of GSTz1/MAAI, an effect accentuated by increased age of the host[33]. Although various human polymorphisms of GSTz1/MAAI were known to exist and to have different affinities for DCA in vitro, the in vivo relationship between genotype and DCA kinetics remained unknown. The present work firmly establishes the significance of GSTz1/MAAI haplotype on the kinetics and biotransformation of DCA in humans. The importance of haplotype is further illustrated by our discovery of a new coding SNP (G→A) in the GSTz1/MAAI gene that was observed in an individual with a profound slowing of DCA plasma clearance and metabolism.

A limitation of this study is the lack of statistical power to determine the impact of each haplotype on DCA metabolism. However, the detailed clinical experimental approach that was necessary to identify haplotype-specific differences in DCA kinetics and biotransformation makes resolution of this issue impracticable by in vivo studies alone. Alternatively, the application of in vitro techniques, such as site-directed mutagenesis, may afford a means by which the differential effects of genetic variants of drug-metabolizing enzymes can be dissected[45].

In addition, our atomic modeling of GSTz1/MAAI provides new mechanistic insight into how polymorphisms affect enzymatic function and DCA clearance rates. The structural consequence of Met residues at position 82 and 99 are striking and are predicted to affect protein stability. In addition, substitution of Met at position 82 may impair GSTz1/MAAI dimerization, because the altered side chain is located at the solvent-accessible surface that is oriented towards the opposing subunit (FIG. 5A). The newly discovered G≥A substitution at position 99 (Val99Met) is predicted to cause a decrease in protein stability that inhibits enzyme activity. Consistent with this notion that effects on protein stability are causally related to perturbation of DCA kinetics is the additional finding that Thr82Met is also associated with a markedly delayed clearance of the drug. Accordingly, persons who are heterozygous (e.g., subjects 11 and 12, Table 1 and patient 5, Table 4) or homozygous (e.g., patient 6, Table 4) for either of these substitutions would be predicted to have very slow rates of DCA kinetics and biotransformation and persistently elevated plasma concentrations of DCA.

Based on in vitro enzyme kinetic studies[2], we originally postulated that the KRT haplotype would also be associated with decreased DCA clearance. In fact, KRT herterozygocity does not appear to affect DCA kinetics when it is paired either with the wildtype EGT allele or with the less common KGT allele, both of which are associated with relatively rapid metabolism of DCA (Table 1). In contrast, KRT homozygosity (subject 10, Table 1) results in a rate of DCA clearance similar to that of persons who possess one or more KGM or EGM alleles. Atomic modeling of the Lys32Glu side chain reveals a potential mechanism for the effect of KRT polymorphism in the GSTz1/MAAI gene involving altered protein-protein interactions of the enzyme.

Our studies also help clarify important relationships between GSTz1/MAAI genotype and DCA toxicity. In general, healthy adult subjects and children with mitochondrial diseases who lack the EGT allele had the highest urinary concentrations of maleylacetone, a substrate of the GSTz1/MAAI-catalyzed step in the tyrosine catabolic pathway. Both maleylacetone and maleylacetoacetate are reactive molecules that can form adducts with proteins and DNA. It is hypothesized that the accumulation of these molecules and related tyrosine intermediates in patients with hereditary tyrosine type 1 is causally related to the hepatotoxicity associated with this disease[29]. Tyrosinemia patients also accumulate increased amounts of succinylacetetone, which inhibits a proximal step in heme synthesis, leading to elevated urinary levels of the heme precursor, delta-aminolevulinate. Both increased delta-aminolevulinate concentrations, per se and/or downstream disruption of heme metabolism have been implicated in the neurotoxicity of tyrosinemia type 1, including peripheral neuropathy[29]. Although no delta-aminolevulinate was detected in the urine of the healthy adult subjects who received 5 days of 25 mg/kg/d DCA, this metabolite was measured in the urine of each of the children who had received the same DCA dose continuously for 12 months, with the highest levels being recorded in the two patients harboring the EGM haplotype (Table 4).

In four adult patients with glioblastoma multiforme who received 6.25 mg/kg DCA twice daily by mouth for at least 3 months, the mean±SD plasma DCA trough concentration was 0.44±0.16 mM (range: 0.27 mM-0.63 mM)[27]. In contrast, the trough level in our 6 children who received 12.5 mg/kg DCA twice daily for 6 months averaged only 0.11±0.11 mM (range: 0.004 mM-0.30 mM), although the trough levels of the 2 subjects who possessed the EGM haplotype were among the highest levels in this group (0.14 mM and 0.30 mM; Table 4). These limited data do not allow valid associations to be made between DCA dosing and its pharmacodynamics. However, it is noteworthy that several of the cancer and mitochondrial disease patients achieved DCA trough levels similar to the 0.2 mM Ki of DCA for the mitochondrial pyruvate dehydrogenase kinase isoform 2 (PDK2)[46]. PDK2 is ubiquitously expressed in tissues and is the principal therapeutic target of DCA relevant to its use in genetic mitochondrial diseases, cancer and pulmonary hypertension. It remains to be determined whether plasma DCA trough levels that approximate the Ki for this isoform becomes a desirable target in future clinical trials with the drug.

Although randomized controlled trials have not described hepatotoxicity from chronic DCA, open label studies have occasionally reported individual cases of asymptomatic and reversible elevations in serum alanine aminotransferase and aspartate aminotransferase concentrations. More problematic is the association of DCA with exacerbation or new onset of reversible peripheral neuropathy. However, such data are difficult to interpret, because patients with mitochondrial diseases are already at high risk for manifesting signs of hepatotoxicity[47] and peripheral neuropathy[48]. In the glioma trial[27], peripheral neuropathy was reported to be moderate to severe at twice daily DCA doses of 12.5 mg/kg-25 mg/kg but minimal to absent at twice daily doses of 6.25 mg/kg.

Our findings also have potentially important implications for populations that are chronically exposed to DCA present in the environment, either through chlorinated drinking water[49] or, less frequently, from water sources contaminated with trichloroethylene or other industrial solvents that are biotransformed to DCA[50]. It has been estimated that the daily consumption of 2 L of chlorinated drinking water provides about 2-4 µg DCA/kg body weight. Short-term oral administration of 2.5 µg/kg/day of $^{13}$C-DCA to healthy subjects is sufficient to cause significant inhibition of DCA plasma clearance (Table 3)[51], albeit to a far lesser degree than does exposure to the clinically relevant doses administered in the present study. Nevertheless, our findings suggest that daily consumption of chlorinated water by individuals whose GSTz1/MAAI genotype confers slow metabolism of DCA could be predisposed to health complications associated with chronic trichloroethylene exposure.

Lastly, our data also suggest that GSTz1/MAAI haplotype may determine flux through the phenylalanine/tyrosine catabolic pathway, thereby influencing an individual's capacity to metabolize a diet containing these amino acids. It would be anticipated, therefore, that persons who metabolize DCA slowly would also metabolize phenylalanine and tyrosine at reduced rates and might be more likely to accumulate potentially toxic tyrosine intermediates, particularly with chronic consumption of a high protein diet. This postulate is amenable to direct clinical experimentation using well-validated procedures for measuring amino acid turnover in humans.

We conclude that the toxicokinetics of DCA can be predicted, at least in part, by knowledge of GSTz1/MAAI genotype and that individuals enrolled in clinical trials of DCA for treatment of mitochondrial diseases, cancer or other conditions who possess at least one KGM or EGM allele may be at heightened risk for developing adverse drug effects, unless dose adjustments are made. Moreover, GSTz1/MAAI genotype may confer added risk to populations who are chronically exposed to environmental levels of DCA or its precursors and/or to chronic consumption of protein-enriched diets.

REFERENCES FOR EXAMPLE 1

1. Stacpoole P W, Henderson G N, Yan Z, Cornett R, James M O. Pharmacokinetics, metabolism and toxicology of dichloroacetate. *Drug Metab Rev* 1998 30:499-539.
2. Stacpoole P W, Kurtz T L, Han Z, Langaee T Y. Role of dichloroacetate in the treatment of genetic mitochondrial diseases. In, *Mitochondrial Medicine and Mitochondrion-Based Therapeutics* published in *Advanced Drug Delivery Reviews* 2008 60:1478-87.
3. Stacpoole P W, Kerr D S, Barnes C, et al. A controlled clinical trial of dichloroacetate for treatment of congenital lactic acidosis in children. *Pediatrics* 2006 117:1519-1531.
4. Cree L M, Samuels D C, Chinnery P F. The inheritance of pathogenic mitochondrial DNA mutations. *Biochim Biophys Acta* 2009 1792:1097-102.
5. Bonnet S, Archer S L, Allalunis-Turner J, et al. A mitochondria-K+ channel axis is suppressed in cancer and its normalization promotes apoptosis and inhibits cancer growth. *Cancer Cell* 2007 11:37-51.
6. Wong J Y, Huggins G S, Debidda M, Munshi N C, De Vivo I. Dichloroacetate induces apoptosis in endometrial cancer cells. *Gynecol Oncol* 2008 109:394-402.
7. Cao W, Yacoub S, Shiverick K T, et al. Dichloroacetate (DCA) sensitizes both wild-type and over expressing Bcl-2 prostate cancer cells in vitro to radiation. *Prostate* 2008 68:1223-1231.
8. Michelakis E D, Webster L, Mackey J R. Dichloroacetate (DCA) as a potential metabolic-targeting therapy for cancer. *Br J Cancer* 2008 99:989-994.
9. Kissling G E, Malarkey D E, Valiant M K, et al. Evaluation of dichloroacetic acid for carcinogenicity in genetically modified Tg.AC hemizygous and p53 haploinsufficient mice. *Toxicol Sci* 2009 107:19-26.
10. Higgins L H, Withers H G, Garbens A, et al. Hypoxia and the metabolic phenotype of prostate cancer cells. *Biochim Biophys Acta* 2009 1787:1433-1443.
11. Sun R C, Fadia M, Dahlstrom J E, Parish C R, Board P G, Blackburn A C. Reversal of the glycolytic phenotype by dichloroacetate inhibits metastatic breast cancer cell growth in vitro and in vivo. *Breast Cancer Res Treat* 2010 120. 253-60.
12. Chen Y, Cairns R, Papandreou I, Koong A, Denko N C. Oxygen consumption can regulate the growth of tumors, a new perspective on the Warburg effect. *PLoS One* 2009 15. e7033.
13. Cairns R A, Bennewith K L, Graves E E, Giaccia A J, Chang D T, Denko N C. Pharmacologically increased tumor hypoxia can be measured by 18F-Fluoroazomycin arabinoside positron emission tomography and enhances tumor response to hypoxic cytotoxin PR-104. *Clin Cancer Res* 2009 15:7170-174.
14. Dhar S, Lippard S J. Mitaplatin, a potent fusion of cisplatin and the orphan drug dichloroacetate. *Proc Natl Acad Sci USA* 2009 106. 22199-204.
15. Anderson K M, Jajeh J, Guinan P, Rubenstein M. In vitro effects of dichloroacetate and CO2 on hypoxic HeLa cells. *Anticancer Res* 2009 29:4579-88.
16. Archer S L, Gomberg-Maitland M, Maitland M L, Rich S, Garcia J G, Weir E K. Mitochondrial metabolism, redox signaling, and fusion: a mitochondria-ROS-HIF-1alpha-Kv1.5 O2-sensing pathway at the intersection of pulmonary hypertension and cancer. *Am J Physiol Heart Circ Physiol* 2008 294:H570-H578.
17. Dromparis P, Sutendra G, Michelakis E D. The role of mitochondria in pulmonary vascular remodeling. *J Mol Med* 2010 88:1003-1010.
18. Piao L, Marsboom G, Archer S L. Mitochondrial metabolic adaptation in right ventricular hypertrophy and failure. *J Mol Med* 2010 88:1011-1020.
19. Sutendra G, Bonnet S, Rochefort G, Haromy A, Folmes K D, Lopaschuk G D, Dyck J R, Michelakis E D. Fatty acid oxidation and malonyl-CoA decarboxylase in the vascular remodeling of pulmonary hypertension. *Sci Trans Med* 2010 2:44ra58.
20. Dunbar E and Stacpoole P W. 2010. Study of the Safety and Efficacy of Dichloroacetate (DCA) in Brain Tumors, University of Florida, ClinicalTrials.gov Identifier: NCT01111097.
21. Garon E. 2009. Phase II Study of Dichloroacetate (DCA) in Patients With Previously Treated Metastatic Breast or NSCL Cancer, University of California, Los Angeles, ClinicalTrials.gov Identifier: NCT01029925.
22. Petruk K, Michelakis E D, Maguire C and Webster L. 2007. The Safety and Efficacy of DCA for the Treatment of Brain Cancer, University of Alberta, ClinicalTrials.gov Identifier: NCT00540176.
23. Venner P and Michelakis E D. 2007. A Phase I, Open-Labeled, Single-Arm, Dose Escalation, Clinical and Pharmacology Study of Dichloroacetate (DCA) in Patients With Recurrent and/or Metastatic Solid Tumours, Alberta Health Services, ClinicalTrials.gov Identifier: NCT00566410.
24. Abdulkarim B. 2008. Combining Radiotherapy and Temozolomide With Dichloracetate in Patients With Newly Diagnosed Glioblastoma, Alberta Health Services, ClinicalTrials.gov Identifier: NCT00703859.
25. Chang D T. 2010. Phase I Trial of Metabolic Reprogramming Therapy for Treatment of Recurrent Head and Neck Cancers, Stanford University, ClinicalTrials.gov Identifier: NCT01163487.
26. Michelakis E D. Personal Communication. 2010.
27. Michelakis E D, Sutendra G, Dromparis P, et al. Metabolic Modulation of Glioblastoma with Dichloroacetate. *Sci Trans Med* 2010 2:31-34.
28. Tong Z, Board P G, Anders M W. Glutathione transferase zeta catalyses the oxygenation of the carcinogen dichloroacetic acid to glyoxylic acid. *Biochem J* 1998 331:371-374.
29. Tanguay R M, Lambert M, Grompe M, Mitchell G A. 2004. Hypertyrosinemia. In, *Metabolic and Molecular Bases of Inherited Disease*. (McGraw-Hill Companies Inc., Chap. 79, pp. 1777-1805).
30. Henderson G N, Curry S H, Derendorf H, Wright E C, Stacpoole P W. Pharmacokinetics of dichloroacetate in adult patients with lactic acidosis. *J Clin Pharmacol* 1997 37:416-425.
31. Ammini C V, Fernandez-Canon J, Shroads A L, et al. Pharmacologic or genetic ablation of maleylacetoacetate isomerase increases levels of toxic tyrosine catabolites in rodents. *Biochem Pharmacol* 2003 66:2029-2038.
32. Kaufmann P, Engelstad K, Wei Y, et al. Dichloroacetate causes toxic neuropathy in MELAS: a randomized, controlled clinical trial. *Neurology* 2006 66:324-30.
33. Shroads A L, Guo X, Dixit V, Liu H-P, James M O, Stacpoole P W. Age-dependent metabolism of dichloroacetate in rats: possible relevance to human toxicity. *J Pharmacol Exper Ther* 2008 324:1163-1171.

34. Blackburn A C, Tzeng H F, Anders M W, Board P G. Discovery of a functional polymorphism in human glutathione transferase zeta by expressed sequence tag database analysis. *Pharmacogenetics* 2000 10:49-57.
35. Uden P C C, Miller J W. Chlorinated acids and chloral in drinking water. *J Amer Water Works Assoc* 1983 75:524-527.
36. Stacpoole P W, Henderson G N, Yan Z, James M O. Clinical pharmacology and toxicology of dichloroacetate. *Environ Health Perspect* 1998 106:989-994.
37. Shroads A L, Henderson G N, Cheung J, James M O, Stacpoole P W. Unified gas chromatographic-mass spectrometric method for quantitating tyrosine metabolites in urine and plasma. *J Chromatogr B Analyt Technol Biomed Life Sci* 2004 808:153-61.
38. Felitsyn N M, Henderson G N, James M O, Stacpoole P W. Liquid chromatography-tandem mass spectrometry method for the simultaneous determination of δ-ALA, tyrosine and creatinine in biological fluids. *Clin Chim Acta* 2004 350:219-30.
39. Paine M F, Wagner D A, Hoffmaster K A, Watkins P B. Cytochrome P450 3A4 and P-glycoprotein mediate the interaction between an oral erythromycin breath test and rifampin. *Clin Pharmacol Ther* 2002 72:524-535.
40. Stephens M, Smith N J, Donnelly P. A new statistical method for haplotype reconstruction from population data. *Am J Hum Genet* 2001 68. 978-989.
41. Nickerson D A, Tobe V O, Taylor S L. PolyPhred: automating the detection and genotyping of single nucleotide substitutions using fluorescence-based resequencing. *Nucleic Acids Res* 1997 25:2745-2751.
42. Rossjohn J, McKinstry W J, Oakley A J, et al. Human theta class glutathione transferase: the crystal structure reveals a sulfate-binding pocket within a buried active site. *Structure* 1998a 6:309-322.
43. Rossjohn J, Polekhina G, Feil S C, et al. A mixed disulfide bond in bacterial glutathione transferase: functional and evolutionary implications. *Structure* 1998b 6:721-734.
44. Kiefer F, Arnold K, Künzli M, Bordoli L, Schwede T. The SWISS-MODEL Repository and associated resources. *Nucleic Acids Res* 2009 37:0387-0392.
45. Zhu H, Patrick K S, Yuan H, et al. Two CES1 gene mutations lead to dysfunctional carboxylesterase 1 activity in man: clinical significance and molecular basis. *Am J Hum Genet* 2008 82:1241-1248.
46. Bowker-Kinley M M, Davis W I, Wu P, Harris R A, Popov K M. Evidence for existence of tissue-specific regulation of the mammalian pyruvate dehydrogenase complex. *Biochem J* 1998 329:191-196.
47. Bindoff L. Mitochondrial Gastroenterology. In, Mitochondrial Medicine, eds. S. DiMauro, M. Hirano, E. A. Schon. informa Healthcare, Abingdon, Ox N, UK. 2006. Pp. 143-159.
48. Stickler D, Valenstein E, Neiberger R E, et al. Peripheral neuropathy in genetic mitochondrial diseases. *Pediatr Neurology* 2006 34:127-131.
49. Chlorinated Drinking-water; Chlorination By-products; Some Other Halogenated Compounds; Cobalt and Cobalt Compounds. (WHO IARC Monographs on the Evaluation of Carcinogenic Risks to Humans Vol. 52, 1991)
50. Lash L H, Fisher J W, Lipscomb J C, Parker J C. Metabolism of Trichloroethylene. *Environ Health Perspect* 2000 108:177-200.
51. Jia M, Wu W W, Yost R A, Chadik P A, Stacpoole P W, Henderson G N. Simultaneous determination of trace levels of nine haloacetic acids in biological samples as their pentafluorobenzyl derivatives by gas chromatography/tandem mass spectrometry in electron capture negative ion chemical ionization mode. *Anal Chemistry* 2003 75:4065-4080.

Example 2

Dichloroacetate (DCA) holds an almost unique position at the interface between environmental science and allopathic medicine, being viewed as both a population health hazard and as a drug of intriguing clinical potential. DCA is dechlorinated by glutathione transferase zeta 1 (GSTz1) that is identical to the penultimate enzyme of the phenylalanine/tyrosine catabolic pathway, maleylacetoacetate isomerase (MAAI). DCA is a suicide inhibitor of GSTz1/MAAI, although its biotransformation is also influenced inversely by age (J Pharmacol Exper Ther. 324:1163-1171, 2008) and by haplotype variation in the GSTz1/MAAI gene (J Clin Pharmacol. In press, 2011, PMID:21642471). Interest in DCA's therapeutic potential has recently intensified, based on reports of its selective pro-apoptotic and anti-proliferative actions in human cancers and in pulmonary arterial hypertension that have led to several early-phase clinical trials. However, the clinically limiting side effect of chronic DCA is reversible peripheral neuropathy. The most common human GSTz1/MAAI haplotypes are EGT (Glu32/Gly42/Thr82), KGT (Lys32/Gly42/Thr82), EGM (Glu32/Gly42/Met82) and KRT (Lys32/Arg42/Thr82). Carriers of the wildtype (EGT) allele have more rapid plasma clearance of DCA than those who are not EGT carriers, as vividly illustrated by the following case comparison. A 68-year-old man with a left frontal lobe glioblastoma multiforme enrolled in a phase I trial of DCA for adults with recurrent brain tumors conducted at the University of Florida, in which retrospective GSTz1 haplotype analysis was an exploratory endpoint. At enrollment, he had ataxia but normal liver and renal function. He received sodium DCA 8 mg/kg body wt/12 hrs by mouth, at which time DCA levels were undetectable in plasma and urine. After 26 days of treatment he presented with worsening gait and DCA was stopped. The patient's GSTz1/MAAI genotype was subsequently found to be EGM/EGM, which, based on previous studies, would predict a very slow rate of plasma drug clearance. Three, 8 and 9 days after DCA was discontinued, the patient's plasma (urine) DCA concentrations (µg/ml) were: 280 (1); 150 (58); and 140 (73). In contrast, a 57-year-old male in the same trial, who was homozygous for the wildtype (EGT) allele and who received the same DCA dose, had trough plasma drug levels of 10.5 and 11.2 µg/ml after 90 and 120 days of continuous drug administration. These data emphasize the importance of prior knowledge of GSTz1/MAAI genotype in assigning dosing regimens to subjects participating in clinical trials of DCA.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%)

within the indicated range. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

the third target substrate comprises a polynucleotide having a sequence corresponding to a wild-type GSTZ1/MAAI;

a fourth target substrate that can detect the presence of the KGT allele in the GSTZ1/MAAI haplotype, wherein the fourth target substrate comprises a polynucleotide having a sequence corresponding to a Glu32Lys mutation in GSTZ1/MAAI; and a fifth target substrate that can detect the presence of the KRT allele in the GSTZ1/MAAI haplotype, wherein the fifth target substrate comprises a polynucleotide having a sequence corresponding to a Gly42Arg mutation in GSTZ1/MAAI.

We claim the following:

1. An array for determining a GSTZ1/MAAI haplotype of a subject comprising:
    a first target substrate that can detect the presence of the KGM allele in the GSTZ1/MAAI haplotype, wherein the first target substrate comprises a polynucleotide having a sequence corresponding to a Val99Met mutation in GSTZ1/MAAI;
    a second target substrate that can detect the presence of the EGM allele in the GSTZ1/MAAI haplotype, wherein the second target substrate comprises a polynucleotide having a sequence corresponding to a Thr82Met mutation in GSTZ1/MAAI;
    a third target substrate that can detect the presence of the EGT allele in the GSTZ1/MAAI haplotype, wherein 2. A kit for treating a disease or disorder with dichloroacetate (DCA), comprising an array of claim 1, directions for use of the array, and directions describing one or more types of GSTZ1/MAAI haplotypes that have a risk of adverse drug effects if given a standard DCA dosing regime.

3. The kit of claim 2, wherein the directions describing one or more types of GSTZ1/MAAI haplotypes includes: reducing the standard DCA dosing regime for a subject having at least one KGM allele in the GSTZ1/MAAI haplotype.

4. The kit of claim 2, wherein the directions describing one or more types of haplotypes includes: reducing the standard DCA dosing regime for a subject having at least one EGM allele in the GSTZ1/MAAI haplotype.

5. The kit of claim 2, wherein the directions describing one or more types of GSTZ1/MAAI haplotypes includes:

reducing the standard DCA dosing regime for a subject not having at least one EGT allele in the GSTZ1/MAAI haplotype.

6. The kit of claim 2, wherein the directions describing one or more types of GSTZ1/MAAI haplotypes includes: reducing the standard DCA dosing regime for a subject having KRT allele homozygosity.

7. A kit for determining if a patient can effectively metabolize one or both of phenylalanine and tryrosine, comprising an array of claim 1 and directions for use of the array, and directions describing one or more types of GSTZ1/MAAI haplotypes that indicate if the subject effectively metabolizes one or both of phenylalanine and tryrosine.

8. The kit of claim 7, wherein the directions describing one or more types of GSTZ1/MAAI haplotypes includes: reducing a standard DCA dosing regime for a subject having at least one KGM allele in the GSTZ1/MAAI haplotype.

9. The kit of claim 7, wherein the directions describing one or more types of GSTZ1/MAAI haplotypes includes: reducing a standard DCA dosing regime for a subject having at least one EGM allele in the GSTZ1/MAAI haplotype.

10. The kit of claim 7, wherein the directions describing one or more types of GSTZ1/MAAI haplotypes includes: reducing a standard DCA dosing regime for a subject not having at least one EGT allele in the STZ1/MAAI haplotype.

11. The kit of claim 7, wherein the directions describing one or more types of GSTZ1/MAAI haplotypes includes: reducing a standard DCA dosing regime for a subject having KRT allele homozygosity.

* * * * *

UNITED STATES PATENT AND TRADEMARK OFFICE
CERTIFICATE OF CORRECTION

PATENT NO. : 9,765,393 B2
APPLICATION NO. : 13/703990
DATED : September 19, 2017
INVENTOR(S) : Langaee et al.

Page 1 of 1

It is certified that error appears in the above-identified patent and that said Letters Patent is hereby corrected as shown below:

At Column 1, Line 20, delete:
"STATEMENT OF GOVERNMENTAL SUPPORT
This invention was made with government support under grant number R01 ES014617-01, awarded by the National Institutes of Health of the United States government. The government has certain rights in the invention."

And replace with:
--STATEMENT REGARDING FEDERALLY SPONSORED RESEARCH OR DEVELOPMENT
The invention was made with government support under Grant No. ES014617 awarded by the National Institutes of Health. The government has certain rights in the invention.--

Signed and Sealed this
Seventh Day of November, 2017

Joseph Matal
*Performing the Functions and Duties of the
Under Secretary of Commerce for Intellectual Property and
Director of the United States Patent and Trademark Office*

SEQUENCE LISTING

```
<160> NUMBER OF SEQ ID NOS: 2

<210> SEQ ID NO 1
<211> LENGTH: 18
<212> TYPE: DNA
<213> ORGANISM: Artificial Sequence
<220> FEATURE:
<223> OTHER INFORMATION: wild-type GSTz1/MAAI (transcript variant 1,
      NM_145870)  r is G in wild-type
<220> FEATURE:
<221> NAME/KEY: misc_feature
<222> LOCATION: (10)..(10)
<223> OTHER INFORMATION: r indicates the position in the wild-type
      sequence where a nucleotide mutation can occur to yeild the V99M
      mutation. r is guanine ("g") in the wild-type sequence

<400> SEQUENCE: 1
agggccagcr tgcgtatg                                                    18

<210> SEQ ID NO 2
<211> LENGTH: 18
<212> TYPE: DNA
<213> ORGANISM: Artificial Sequence
<220> FEATURE:
<223> OTHER INFORMATION: Mutatant NM_145870 where position 259 of exon
      5 of GSTz1MAA1 is mutated (n is A, to generate V99M mutation)
<220> FEATURE:
<221> NAME/KEY: mutation
<222> LOCATION: (10)..(10)
<223> OTHER INFORMATION: n is adenine ("a") in the mutation
<220> FEATURE:
<221> NAME/KEY: misc_feature
<222> LOCATION: (10)..(10)
<223> OTHER INFORMATION: n is a, c, g, or t

<400> SEQUENCE: 2
agggccagcn tgcgtatg                                                    18
```